US008986238B2

(12) United States Patent  
Robinson

(10) Patent No.: US 8,986,238 B2
(45) Date of Patent: Mar. 24, 2015

(54) SYSTEMS AND METHODS FOR SALVAGING RED BLOOD CELLS FOR AUTOTRANSFUSION

(71) Applicant: Cyclone Medtech, Inc., St. Paul, MN (US)

(72) Inventor: Len Robinson, Brooklyn Park, MN (US)

(73) Assignee: Cyclone Medtech, Inc., St. Paul, MN (US)

( * ) Notice: Subject to any disclaimer, the term of this patent is extended or adjusted under 35 U.S.C. 154(b) by 0 days.

(21) Appl. No.: 13/966,916

(22) Filed: Aug. 14, 2013

(65) Prior Publication Data

US 2014/0050615 A1     Feb. 20, 2014

Related U.S. Application Data

(60) Provisional application No. 61/683,315, filed on Aug. 15, 2012.

(51) Int. Cl.
*A61M 1/36*     (2006.01)
*B30B 9/04*     (2006.01)
*A61M 1/02*     (2006.01)

(52) U.S. Cl.
CPC ............... *B30B 9/04* (2013.01); *A61M 1/0281* (2013.01)
USPC .......................................... 604/6.09

(58) Field of Classification Search
CPC ........ A61B 19/00; A61M 1/0281; B30B 9/04
USPC .......................................... 600/371
See application file for complete search history.

(56) References Cited

U.S. PATENT DOCUMENTS

| 1,886,578 A | 11/1932 | Pedrazzo |
| 3,706,412 A | 12/1972 | Latham |
| 3,749,285 A | 7/1973 | Latham |
| 3,768,653 A | 10/1973 | Brumfield |
| 3,785,549 A | 1/1974 | Latham |
| 3,831,813 A | 8/1974 | Latham |

(Continued)

FOREIGN PATENT DOCUMENTS

| CN | 2602043 | 2/2002 |
| EP | 0573117 | 8/1998 |

(Continued)

OTHER PUBLICATIONS

File History for U.S. Appl. No. 13/966,906.

(Continued)

*Primary Examiner* — Susan Su
(74) *Attorney, Agent, or Firm* — Kinney & Lange, P.A.

(57) ABSTRACT

Systems and methods for salvaging blood cells from an absorbent material are disclosed. In one exemplary aspect, such as system includes a rotatable basin having perforations to allow rinse solution from a stationary basin to reversibly flow therethrough to wash the blood cells from the absorbent material, thereby forming an effluent solution. The system further includes a hemoconcentrator in fluid communication with the stationary basin having first and second fluid outputs for discharging a diluent solution and a blood cell discharge solution from the effluent solution respectively. The blood cells can be salvaged from the blood cell discharge solution. The second fluid output is in fluid communication with the stationary basin for recycling the diluent solution as the rinse solution.

28 Claims, 5 Drawing Sheets

(56) References Cited

U.S. PATENT DOCUMENTS

| | | | |
|---|---|---|---|
| 3,916,892 | A | 11/1975 | Latham, Jr. |
| 3,965,896 | A | 6/1976 | Swank |
| 4,033,345 | A | 7/1977 | Sorenson et al. |
| 4,054,523 | A | 10/1977 | Ingenito et al. |
| 4,059,108 | A | 11/1977 | Latham, Jr. |
| 4,086,924 | A | 5/1978 | Latham, Jr. |
| 4,115,277 | A | 9/1978 | Swank |
| 4,204,537 | A | 5/1980 | Latham, Jr. |
| 4,243,531 | A | 1/1981 | Crockett et al. |
| 4,285,464 | A | 8/1981 | Latham, Jr. |
| 4,300,717 | A | 11/1981 | Latham, Jr. |
| 4,303,193 | A | 12/1981 | Latham, Jr. |
| 4,304,357 | A | 12/1981 | Schoendorfer |
| 4,381,776 | A | 5/1983 | Latham, Jr. |
| 4,385,630 | A | 5/1983 | Gilcher et al. |
| 4,402,680 | A | 9/1983 | Schoendorfer |
| 4,405,079 | A | 9/1983 | Schoendorfer |
| 4,416,654 | A | 11/1983 | Hansen et al. |
| 4,417,884 | A | 11/1983 | Latham, Jr. et al. |
| 4,421,506 | A | 12/1983 | Danby et al. |
| 4,425,114 | A | 1/1984 | Lueptow et al. |
| 4,445,883 | A | 5/1984 | Schoendorfer |
| 4,464,167 | A | 8/1984 | Hansen et al. |
| 4,466,888 | A | 8/1984 | Verkaart |
| 4,474,568 | A | 10/1984 | Kingsley et al. |
| 4,480,751 | A | 11/1984 | Lueptow |
| 4,482,342 | A | 11/1984 | Lueptow et al. |
| 4,531,954 | A | 7/1985 | Klein |
| 4,561,868 | A | 12/1985 | Vizulis et al. |
| 4,673,423 | A | 6/1987 | Yumlu |
| 4,681,677 | A | 7/1987 | Kuh et al. |
| 4,704,203 | A | 11/1987 | Reed |
| 4,740,202 | A | 4/1988 | Headley et al. |
| 4,743,371 | A | 5/1988 | Gremel et al. |
| 4,755,300 | A | 7/1988 | Brumfield et al. |
| 4,758,337 | A | 7/1988 | Kohn et al. |
| 4,767,396 | A | 8/1988 | Powers |
| 4,795,448 | A | 1/1989 | Headley et al. |
| 4,808,307 | A | 2/1989 | Brumfield et al. |
| 4,871,453 | A | 10/1989 | Kumar |
| 4,886,487 | A * | 12/1989 | Solem et al. ............. 604/6.07 |
| 4,889,524 | A | 12/1989 | Fell et al. |
| 4,898,572 | A | 2/1990 | Lasnier et al. |
| 4,943,273 | A | 7/1990 | Pages |
| 4,954,251 | A | 9/1990 | Barnes et al. |
| D312,128 | S | 11/1990 | Headley |
| 4,983,158 | A | 1/1991 | Headley |
| 5,015,388 | A | 5/1991 | Cronenberger et al. |
| 5,045,048 | A | 9/1991 | Kaleskas et al. |
| 5,055,198 | A * | 10/1991 | Shettigar ....................... 210/650 |
| 5,100,372 | A | 3/1992 | Headley |
| 5,133,703 | A | 7/1992 | Bence et al. |
| 5,135,645 | A | 8/1992 | Aisenberg et al. |
| 5,149,318 | A | 9/1992 | Lindsay |
| 5,183,569 | A | 2/1993 | Kyriacou |
| 5,215,519 | A | 6/1993 | Shettigar |
| 5,223,154 | A | 6/1993 | MacPherson, Jr. |
| 5,273,517 | A | 12/1993 | Barone et al. |
| 5,304,164 | A | 4/1994 | Lindsay |
| 5,311,908 | A | 5/1994 | Barone et al. |
| 5,348,533 | A | 9/1994 | Papillon et al. |
| 5,387,088 | A | 2/1995 | Baruch et al. |
| 5,387,187 | A | 2/1995 | Fell et al. |
| 5,399,156 | A | 3/1995 | Lindsay |
| 5,405,308 | A | 4/1995 | Chammas et al. |
| 5,411,705 | A | 5/1995 | Dando et al. |
| 5,423,738 | A | 6/1995 | Appleby et al. |
| 5,458,459 | A | 10/1995 | Clausen et al. |
| 5,458,566 | A | 10/1995 | Anderson et al. |
| 5,478,479 | A | 12/1995 | Herrig |
| 5,494,592 | A | 2/1996 | Jorgensen et al. |
| 5,505,683 | A | 4/1996 | Geringer et al. |
| 5,514,070 | A | 5/1996 | Pages |
| 5,514,095 | A | 5/1996 | Brighbill et al. |
| D377,685 | S | 1/1997 | Carr, Jr. et al. |
| 5,607,579 | A | 3/1997 | Jorgensen et al. |
| 5,634,893 | A | 6/1997 | Rishton |
| 5,637,082 | A | 6/1997 | Bernt et al. |
| 5,643,193 | A | 7/1997 | Pages et al. |
| 5,658,231 | A | 8/1997 | Chammas et al. |
| 5,674,173 | A | 10/1997 | Hlavinka et al. |
| 5,681,709 | A | 10/1997 | Mochnal et al. |
| 5,725,777 | A | 3/1998 | Taylor |
| 5,769,811 | A | 6/1998 | Lamborghini et al. |
| 5,770,073 | A | 6/1998 | Bach et al. |
| 5,783,093 | A | 7/1998 | Holme |
| 5,791,592 | A | 8/1998 | Nolan et al. |
| 5,800,721 | A | 9/1998 | McBride |
| 5,879,624 | A | 3/1999 | Boehringer et al. |
| 5,882,289 | A | 3/1999 | Ohashi et al. |
| 5,954,971 | A | 9/1999 | Baratelli et al. |
| 5,971,948 | A | 10/1999 | Pages et al. |
| 6,026,684 | A | 2/2000 | Calder |
| D423,095 | S | 4/2000 | Chammas et al. |
| 6,099,493 | A | 8/2000 | Swisher |
| 6,113,554 | A | 9/2000 | Chammas et al. |
| 6,193,681 | B1 * | 2/2001 | Davidner et al. ............ 604/6.08 |
| 6,250,331 | B1 | 6/2001 | Nardi |
| 6,251,291 | B1 | 6/2001 | Lamphere et al. |
| 6,267,925 | B1 | 7/2001 | Pages |
| 6,402,702 | B1 | 6/2002 | Gilcher et al. |
| 6,440,372 | B1 | 8/2002 | Pages |
| 6,464,624 | B2 | 10/2002 | Pages |
| 6,558,307 | B2 | 5/2003 | Headley |
| 6,558,341 | B1 | 5/2003 | Swisher |
| 6,602,179 | B1 | 8/2003 | Headley et al. |
| 6,629,919 | B2 | 10/2003 | Egozy et al. |
| 6,632,191 | B1 | 10/2003 | Headley et al. |
| 6,641,552 | B1 | 11/2003 | Kingsley et al. |
| 6,705,983 | B1 | 3/2004 | Rochat |
| 6,709,377 | B1 | 3/2004 | Rochat |
| 6,824,506 | B1 | 11/2004 | Lamphere et al. |
| 6,878,545 | B2 * | 4/2005 | Deckwer et al. ............. 435/366 |
| 6,964,646 | B1 | 11/2005 | Biesel |
| 7,055,401 | B2 | 6/2006 | Luyo et al. |
| 7,063,816 | B2 | 6/2006 | Maianti et al. |
| RE39,449 | E | 12/2006 | Pages |
| 7,332,125 | B2 | 2/2008 | Cianci et al. |
| 7,452,322 | B2 | 11/2008 | Headley et al. |
| 7,601,268 | B2 | 10/2009 | Ragusa |
| D609,334 | S | 2/2010 | Cameron et al. |
| D632,792 | S | 2/2011 | Cameron et al. |
| 8,105,422 | B2 * | 1/2012 | Betting et al. .................. 95/261 |
| 8,157,103 | B2 | 4/2012 | Eagle et al. |
| 8,157,775 | B2 | 4/2012 | Bobroff et al. |
| 8,157,792 | B2 | 4/2012 | Bobroff et al. |
| 2006/0282109 | A1 | 12/2006 | Jansen et al. |
| 2009/0259161 | A1 * | 10/2009 | Ghelli et al. ................. 604/5.03 |
| 2010/0234788 | A1 | 9/2010 | Pages et al. |
| 2010/0236012 | A1 | 9/2010 | Horne |
| 2010/0292628 | A1 | 11/2010 | Murphy et al. |
| 2011/0026009 | A1 | 2/2011 | Akcakir et al. |
| 2011/0068061 | A1 | 3/2011 | Eagle et al. |
| 2011/0178453 | A1 | 7/2011 | Pages et al. |
| 2011/0281346 | A1 | 11/2011 | Costello et al. |
| 2012/0165642 | A1 | 6/2012 | Krensky et al. |
| 2012/0168377 | A1 | 7/2012 | Eagle et al. |
| 2012/0189711 | A1 | 7/2012 | Greenberg et al. |
| 2013/0304020 | A1 * | 11/2013 | Wilt et al. ..................... 604/506 |

FOREIGN PATENT DOCUMENTS

| | | |
|---|---|---|
| EP | 0771570 | 4/2002 |
| WO | WO0038756 | 7/2000 |
| WO | WO2004105838 | 4/2005 |
| WO | WO2012083412 | 6/2012 |

OTHER PUBLICATIONS

Waters, "Intraoperative Blood Conservation—Every Cell is Sacred", ITACCS, Summer 2005, pp. 144-148.
Haemonetics, "Cell Saver 5+ Autologous Blood Recovery System", printed from internet on Aug. 14, 2013.

(56) References Cited

OTHER PUBLICATIONS

Ahmed, "Application of Hydrocyclone for Cell Separation in Mammalian Cell Perfusion Cultures", 2005, 150 pages.

Ronai et al., "Improving Autologous Blood Harvest: Recovery of Red Cells from Sponges and Suction", Anaesth Intensive Care 1987, 15, pp. 421-424.

U.S. Appl. No. 13/966,906, filed Aug. 14, 2013, Robinson.

International Search Report and Written Opinion dated Nov. 18, 2013 from PCT Application No. PCT/US2013/054920, 12 pages.

International Search Report and Written Opinion dated Nov. 18, 2013 from PCT Application No. PCT/US2013/054921, 13 pages.

Dyakowski et al., "A Three Dimensional Simulation of Hydrocyclone Behaviour", Second International Conference on CFD in the Minerals and Process Industries, CSIRO, Melbourne, Australia, Dec. 6-8, 1999, pp. 205-210.

* cited by examiner

SYSTEMS AND METHODS FOR SALVAGING RED BLOOD CELLS FOR AUTOTRANSFUSION

CROSS REFERENCE TO RELATED APPLICATIONS

This application claims the benefit of Provisional Patent Application Ser. No. 61/683,315, entitled "SYSTEMS AND METHODS FOR BLOOD RECOVERY FROM ABSORBENT SURGICAL MATERIALS" filed on Aug. 15, 2012, to which priority is claimed pursuant to 35 U.S.C. §119(e) and which is hereby incorporated herein by reference in its entirety

TECHNICAL FIELD

This disclosure relates to systems and methods for recapturing blood cells for autotransfusion during surgical procedures.

BACKGROUND

Autotransfusion is a surgical practice in which a person receives their own transfused blood instead of banked donor blood. This process can reduce the risk of infection from banked blood supplies such as HIV, hepatitis C, cytomegalovirus, bacterial contamination and other transmissible infections and is commonly used in intraoperative and post-operative situations where the use of homologous blood is contraindicated. Transfusion with banked blood supplies can increase the risk of acute or delayed hemolytic reactions, allergic reactions, post-transfusion purpura and transfusion-associated acute lung injury (TRALI). In addition, some patients refuse transfusion with banked blood due to philosophical differences or spiritual beliefs.

The use of autotransfusion can be particularly beneficial where the patient is at risk of losing one or more units of blood during surgery, in cases involving rare blood types, or where the risk of infectious disease transmission is high. Certain types of surgery, e.g., joint replacements, aneurism, or spinal repair are known to produce proportionally larger blood loss than other types of surgery. Thus, the use of autotransfused blood in these circumstances can be particularly beneficial.

Certain devices are capable of collecting blood from the surgical field, separating viable red blood cells from plasma, platelets, white cells, anticoagulants, and other substances, and re-introduce the red blood cells into the patient. One such device is produced by Haemonetics Corp. of Braintree, Mass., and sold under the "Cell Saver"™ brand.

SUMMARY

Practitioners of the surgical arts will recognize that in some cases large amounts of patient blood can be lost in absorbent materials used during surgery. Doctors, nurses, and other operating room personnel use sponges, gauze, pads, and other materials during and after surgery to control bleeding and to keep the surgical field clear for those performing the surgery. This blood, which may be viable, could be autotransfused to the benefit of the patient. In one general aspect, systems and methods for recovering viable blood cells from absorbent surgical or trauma materials are disclosed. In general, viable blood cells can be recovered from absorbent surgical or trauma materials that may otherwise be discarded.

In one embodiment, a blood salvage device (BSD) includes a porous basin for receiving absorbent surgical or trauma materials. The absorbent surgical or trauma materials can be rinsed with a suitable solution, e.g., saline or heparinized saline to create an effluent composition including the rinse solution and red blood cells. The BSD further includes a hemoconcentrator capable of receiving the effluent and separating red blood cells from the rinse solution. The BSD further includes an effluent plumbing assembly configured in part to return rinse solution to the porous basin to be recycled for further rinsing and to flow red blood cells to the patient for autotransfusion or to a cell salvage machine for further purification.

In one exemplary aspect, an assembly for salvaging blood cells within an absorbent material is disclosed. The assembly includes a first basin having perforations to allow a rinse solution to wash said blood cells from said absorbent material into a second basin to form an effluent solution. The assembly further includes a hemoconcentrator in fluid communication with the second basin having first and second fluid outputs for discharging a diluent solution and a blood cell discharge solution from the effluent solution respectively. The second fluid output is in fluid communication with the second basin for recycling the diluent solution as rinse solution.

In one embodiment, the hemoconcentrator is a hydrocyclone-based particle separator.

In one embodiment, a lumen-interconnected fluid flow circuit is defined from the second basin, to the hemoconcentrator, to second basin, wherein the fluid flow is engendered by a pump.

In one embodiment, the first fluid output of the hemoconcentrator is in fluid communication with an intraoperative cell salvage machine.

In one embodiment, the absorbent material is an absorbent material used for surgical operations or trauma treatment. In a related embodiment, the absorbent material is a sponge, gauze, pad, towel, tape, or felt.

In one embodiment, the assembly further includes an elongate rotor having a first rotor portion fixedly attached to a center of mass of the first basin that defines an axis of rotation about which the first basin can axially rotate.

In one embodiment, the assembly further includes a handle coupled to a proximal portion of the elongate rotor configured to engender rotation of the first basin when the handle is rotated.

In one embodiment, the assembly further includes a motor configured to rotate the rotor about the axis of rotation. In a related embodiment, the motor is configured to couple to a proximal end portion of the rotor.

In one embodiment, the assembly further includes a propeller fixedly coupled to a distal end of the rotor that is configured to flowingly urge effluent solution from the second basin to the hemoconcentrator.

In one embodiment, the first basin is capable of reversibly shifting along the axis of rotation to reversibly remove the absorbent materials from the rinse solution.

In one embodiment, the first basin and the propeller are configured to be selectably rotatable in the same or opposite rotation directions. The rotation speed of each of the first basin and the propeller can be independently controllable.

In one embodiment, the rotor is a coaxial dual-rotor assembly having an inner rotor and an outer rotor each capable of independent, coaxial rotation, and wherein the inner rotor is coupled to the first basin or the propeller, and the outer rotor is coupled to the first basin or the propeller.

In one embodiment, the assembly further includes a valve member in fluid communication with the first fluid output of the hemoconcentrator that is operable to direct the blood cell discharge solution into one of a plurality of fluid flow passages, wherein a first fluid flow passage is configured to flow the blood cell discharge solution from the valve member to an intraoperative cell salvaging machine.

In one embodiment, a second fluid flow passage is configured to flow the blood cell discharge from the valve member to a blood filter. In a related embodiment, the blood filter is a microporous membrane blood filter.

In one embodiment, the second fluid flow passage further includes an in-line de-heparinization chamber for removing heparin, if present, from the blood cell discharge solution downstream from the blood filter. In a related embodiment, the de-heparinization chamber includes a charged porous polymer material for removing heparin. In a further related embodiment, the porous polymer material includes chitosan microspheres.

In one embodiment, the assembly further includes a chamber having a reversibly sealable lid member configured to substantially enclose the stationary basin and the first basin. In a related embodiment, the lid member includes a vacuum port cooperatively operable with a vacuum source to lower the atmospheric inside said chamber when said lid is in a sealed configuration. In a further related embodiment, the lid member further includes one or more accessory suction ports configured to couple to a suction device for vacuuming blood into the chamber. In yet a further related embodiment, the suction device is a suction catheter. In yet a further embodiment, the lid further includes a lumen for introducing the rinse solution into the chamber when the lid is in a sealed configuration. In yet a further embodiment, the lid further includes a perforated, annular and circumferential lumen configured to receive the rinse solution and produce a flow of the rinse solution substantially along the inner walls of the chamber.

In another exemplary aspect, an assembly for salvaging blood for direct patient autotransfusion is disclosed. The assembly includes a wash basin configured to retain a volume of blood-releasing rinse solution and house a portion of a rotatable perforated basin for receiving absorbent materials comprising the patient's blood. The assembly further includes a hemoconcentrator assembly in fluid flow communication with the wash basin capable of substantially separating red blood cells of the patient's blood from the rinse solution to form a first red blood cell discharge solution comprising the red blood cells and a first diluent solution comprising the rinse solution. The assembly further includes a disinfection chamber in fluid flow communication with the hemoconcentrator configured to receive the red blood cell discharge, and comprising a light source capable of emitting an effective dose of electromagnetic radiation to substantially sterilize the red blood cell discharge solution.

In one embodiment, the fluid flow is engendered by a pump.

In one embodiment, the fluid flow is engendered by a propeller operatively disposed within the wash basin. In a related embodiment, the propeller is coupled to a first portion of a rotor that extends through, and is coupled to a center of gravity of the rotatable perforated basin at a second, different portion of the rotor so that the propeller and the rotatable perforated basin share a common axis of rotation.

In one embodiment, the first diluent solution is flowed via a first lumen to the wash basin for re-use as the rinse solution.

In one embodiment, the light source is capable of emitting ultraviolet light. In a related embodiment, the ultraviolet light is ultraviolet-C light.

In one embodiment, the assembly further includes a dilution chamber in fluid communication between the hemoconcentrator and the disinfection chamber for diluting the concentration of red blood cells in the red blood cell supply discharge solution.

In one embodiment, the assembly further includes a second hemoconcentrator in fluid communication with the disinfection chamber that is configured to receive the sterilized red blood cell discharge solution, and further configured to create a second red blood cell supply discharge solution and a second diluent solution from the sterilized red blood cell discharge solution, wherein the second diluent solution is in fluid communication with the wash basin.

In one embodiment, the hemoconcentrator is a hydrocyclone-based particle separator.

In yet another exemplary aspect, an assembly for salvaging a patient's blood cells from absorbent surgical or trauma materials is disclosed. The assembly includes a rotatable, perforated basin for holding the absorbent surgical or trauma materials, an elongate rotor extending through, and coupled to a center of gravity of the rotatable perforated basin, a propeller coupled to a distal end of the rotor, and a wash basin capable of receiving the propeller and at least a portion of the rotatable, perforated basin. The wash basin is also configured to retaining a volume of rinse solution, wherein the rinse solution is capable of substantially releasing blood cells from the absorbent surgical or trauma materials to form an effluent solution. The assembly further includes a housing for enclosing the wash basin, the propeller, and the perforated basin configured to receive a reversibly sealable lid member through which a proximal end of the rotor extends to couple to a motor or hand crank for spinning the propeller and the rotatable perforated basin. The assembly further includes a hydrocyclone-based particle separator in fluid-flow communication with the wash basin that is configured to separate the effluent solution into a red blood cell discharge solution comprising the red blood cells and a diluent solution comprising rinse solution. In this assembly, the red blood cell discharge solution can be salvaged for autotransfusion; the diluent solution is in fluid communication with the wash basin via one or more lumen passages to be re-used as the rinse solution; and spinning the propeller engenders the fluid flow.

The systems and methods described herein provide certain distinct advantages. One advantage includes the ability to salvage blood cells from absorbent materials used during surgery that might otherwise be discarded. Another advantage includes providing a safe method for extracting blood from absorbent materials used during surgery wherein the risk of transmitting a blood-borne disease to surgical staff is minimized. Another advantage includes providing a system for safely disposing of blood-soaked absorbent materials as an alternative to discarding the materials in a trash basin. Yet another advantage includes improvement in the accuracy of determining patient blood loss during surgery. Yet another advantage is that the systems and methods disclosed herein can be used or carried out by any member of a surgical team, e.g., scrub technician, scrub nurse, surgeon without requiring extensive training or a trained technician. Other advantages will be apparent to those skilled in the art of surgery and medical devices for salvaging blood.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, the drawings are not necessarily to scale, and in which.

DETAILED DESCRIPTION OF ILLUSTRATIVE EMBODIMENTS

Systems and methods for recovering blood cells for autotransfusion are disclosed. In general and without limitation, the systems and methods described herein can be applicable in surgical or trauma treatment settings, where it can be beneficial to salvage as much of a patient's red blood cells as possible during operative or treatment procedures. Exemplary surgical settings can include, without limitation, inpatient planned operations such as joint replacements, aneurism, or spinal surgeries where large blood losses may be expected. Surgical settings can also include unplanned operative procedures, e.g., those resulting from trauma where blood loss may be a significant factor in patient survivability. "Patients" can include human and non-human (e.g., veterinary) surgical or trauma subjects. As is generally known in the surgical arts, autotransfusion can aid in patient recovery and reduce the likelihood of infection or other deleterious effects that can result from the use of banked allogenic blood supplies. Autotransfusion may be critical to survivability for patients having rare blood types or when banked blood is in short supply.

In many surgeries or during trauma treatment, absorbent materials, e.g., sponges, towels, pads, etc., are used to soak up a patient's blood. Despite its potential viability, blood absorbed in such materials is seldom—if ever—recovered for the patient, putting a greater demand on the use of banked blood supplies. Thus, a blood salvage device capable of safely recovering patient blood from absorbent surgical or trauma materials for autotransfusion would be beneficial.

Figure 1:
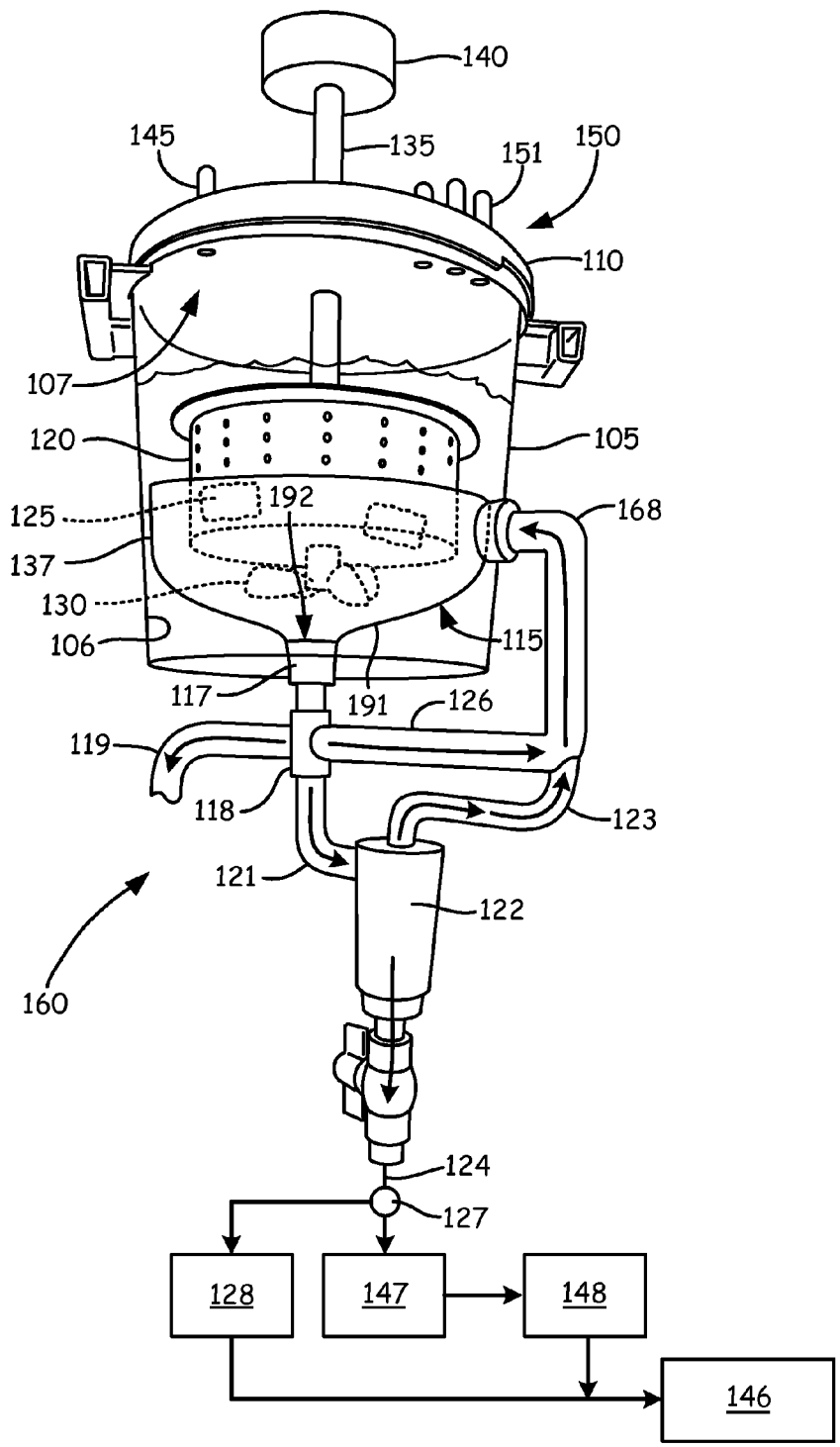
FIG. 1 is a blood salvage device (BSD) according to one embodiment.

Referring now to FIG. 1, a blood salvage device (hereinafter "BSD") 100 is shown according to one embodiment. The BSD 100 is capable of effectively salvaging blood for autotransfusion and is easy and cost-effective to operate. The BSD 100 can be operated in one of several modes to accommodate desired autotransfusion functionality as described in greater detail below, and is modular in design to provide simple assembly and disassembly for cleaning and sterilization between uses. In the detailed description of the BSD 100 that follows, it should be understood that various modifications or substitutions can be made without departing from the spirit and scope of the inventive concept. Furthermore, any description of the use of the BSD 100 are exemplary and non-limiting, with the knowledge that practitioners of the surgical arts, technicians, nurses, or other persons who utilize the BSD 100 may prefer other practice methods or approaches than those described herein.

In this embodiment, the BSD 100 includes an outer chamber 105 configured to enclose other BSD elements as described below. In this embodiment, the outer chamber 105 is cylindrically-shaped and formed of a resilient, transparent thermoplastic such as that sold under the Plexiglass™ brand, although the chamber 105 can be of a different shape or formed of a different material as desired. In this and other embodiments, the outer chamber 105 or other components of the BSD 100 can be configured to allow measurement of collected blood and other fluids from the absorbent materials. An accurate determination of blood loss during surgery can be an important factor in patient care, as is well known in the surgical arts. Thus, in this and other embodiments, the outer chamber 105 can include, for example, graduated markings that demarcate selected volumes and allows a user to measure blood and fluids collected from the absorbent materials by visual reference. The graduated markings can be placed, e.g., on the side of the chamber 105 beginning at the bottom and extending vertically, toward the top.

In this embodiment, the outer chamber 105 includes a top portion 107 configured to sealingly receive a lid member 110. The top portion 107 can be configured to reversibly seal with the lid member 110 by methods known in the art. For example, the top portion 107 can include a recessed annular ring portion configured to receive an O-ring, and the lid member 110 can sealingly engage the top portion 107 through one or more clamps or other devices configured to engage the lid member 110 to the top portion 107 via clamping pressure. Other systems and methods can be used to engage the lid member 110 to the top portion 107. For example, the lid member 110 can include a male-threaded bottom portion (not shown in FIG. 1) configured to thread onto a complimentary female-threaded collar portion (not shown in FIG. 1) near the top portion 107. In another example, the lid member 110 can be secured to the top portion 107 in a sealingly engaged configuration through one or more clamping mechanisms (not shown in FIG. 1). In another example, the lid member 110 can be hingedly coupled to the outer chamber 105, thereby allowing the lid member 110 to pivotally swing open and closed, and be sealingly engaged in the closed configuration during rinsing operations as described below. Other systems and methods will be apparent to skilled artisans.

In this embodiment, the lid member 110 includes a vacuum port 145. The vacuum port 145 in this embodiment is a hollow tube that extends through the lid member 110 and is configured to connect to an external vacuum source (such as those commonly found in operating rooms) to lower the pressure within the outer chamber 105 for suction purposes as described in greater detail below.

In this embodiment, the lid member 110 includes a plurality of suction ports 150. Each suction port, e.g., suction port 151 can be configured to attach to a lumen (not shown in FIG. 1) or other tube-like structure for the purpose of drawing blood or other fluids into the outer chamber 105 when a vacuum source is attached to the vacuum port 145. Each of the suction ports can be individually configured to attach to certain types of lumens or other suction devices, e.g., suction devices used in surgical settings such as a suction catheter. In one embodiment, the suction device is a Yankauer suction catheter. In one embodiment, at least one of the plurality of suction ports 150 is configured as a fill port to allow a rinse solution, e.g., heparinized saline, to be introduced into an inner basin 115 described below. In one embodiment, the lid can include, or can be configured with a circumferential, perforated channel in fluid communication with the fill port to allow rinse solution to wash down the inner side wall 106 of the chamber 105.

In this and other embodiments, "in fluid communication" implies that fluid can flow between a first object and a second object (as described here, between the perforated channel and the fill port) using any type of lumen, plumbing, channel, conduit, or any other material or body capable of supporting the flow of fluid. It should be understood that a wide range of plumbing options are available, some which may be more advantageous in use than others; thus, any description referring to "lumens," "conduits," "fluid passages" and the like are illustrative only and not meant to be limiting with respect to the claims.

In this and other embodiments, the rinse solution used to wash blood from absorbent materials can be of a preferred formulation. For example, a rinse solution can be a saline solution. In another example, the rinse solution can be an aqueous solution including one or more anticoagulants such as citrates, heparin and its derivatives, coumarins, acenocoumarol, phenprocoumon, atromentin, phenindione, or any other additive.

It should be understood that various other substitutions and alternatives can be used to provide the capability of rinsing blood from absorbent materials within the chamber 105. For example, a spigot (not shown in FIG. 1) can be integral with, or removably attached to the chamber 105 or the lid member 110 which can be selectively controlled by a user to flow rinse solution over the absorbent materials.

In this embodiment, the BSD 100 includes a rotatable, perforated retaining basin 120 capable of receiving absorbent surgical or trauma materials therein. Absorbent surgical or trauma materials can include, without limitation, sponges, e.g., sponge 125, towels, gauze, tape, cloth, felt, or any other material capable of absorbing blood or bodily fluids, including materials made from natural or synthetic fibers, or a blend of both. Exemplary absorbent materials include, without limitation, Cottonoid™, provided by Codman and Shurtleff, Inc., Raynham, Mass., USA; Spetzler Neruo Patties, provided by OMT, LLC, Ft. Lauderdale, Fla., USA; and Ray-Tec™ X-Ray-Detectable Sponges, Johnson & Johnson Wound Management, New Brunswick, N.J.

In this embodiment, the perforated retaining basin 120 is formed of perforated stainless steel, although other suitable materials may be substituted as desired. In general, it can be advantageous if the retaining basin 120 and other components of the BSD 100 are formed of a material or materials that are capable of withstanding heat, exposure to disinfecting chemicals, and disinfecting irradiation, e.g., ultraviolet light so that they can be cleansed, disinfected, and reused. In general, the size of the perforations in the retaining basin 120 can be selected to allow fluids such as blood and rinse solution to pass therethrough while substantially retaining the absorbent surgical or trauma materials within the interior portion of the retaining basin 120.

In this embodiment, the retaining basin 120 is configured to be selectively moved up or down as desired, as indicated by the double-headed arrow at the top of the basin. The retaining basin 120 is also configured to be rotated (spun) about an axis generally defined by an elongate rotor 135 which is coupled to, and runs through the center of the circular floor of the retaining basin 120 as illustrated.

In this embodiment, a portion of the rotor 135 is coupled to the floor of the retaining basin 120, such that rotation of the rotor 135 causes synchronous rotation of the retaining basin 120. The retaining basin 120 can be selectively shifted up or down by, e.g., lifting or lowering the rotor 135 respectively. In one embodiment, the BSD 100 includes guide rails or other members (not shown in FIG. 1) attached to, e.g., a portion of the lid member 110, or a portion of the chamber 105 to guide the retaining basin 120 along a vertical pathway.

In this embodiment, the rotor 135 also extends through the lid member 110 and is coupled at a proximal end to a handle 140. The handle 140 can be configured to allow hand-operated rotation of the rotor 135 to cause the basin 120 to spin. For example, a knob handle can allow a user to grasp the knob of the handle and rotate the rotor 135 without requiring repositioning of the hand.

In an alternative embodiment, the handle 140 can be substituted with an electric motor capable of causing the rotor 135 to rotate at a desired angular velocity. One exemplary, non-limiting motor for such purpose is an AC servo motor, model no. EMG-10APA22, available from Anaheim Automation, Anaheim, Calif. In general, the selected motor should be capable of spinning the retaining basin 120 fast enough to extract blood and other liquids from the absorbent surgical or trauma materials through centrifugal force. However, it can be advantageous to incorporate a user-controlled motor speed selector, so that the angular velocity of the basin 120 can be rotated at a speed that minimizes the likelihood of hemolysis.

In this embodiment, the BSD 100 includes a stationary inner basin 115. In this embodiment, the inner basin 115 is configured to retain a bath of rinse solution and fluids that flow out of the retaining basin 120 by way of fluid migration, gravity or centrifugal force. The inner basin 115 can be configured to fit snuggly against the inner wall 106 of the outer chamber 105 so that fluid leaks are minimized therebetween. In this embodiment, the inner basin 115 has a substantially trapezoidal cross section as illustrated, wherein an upper rim 137 of the basin 115 sealingly abuts the inner wall 106 of the outer chamber 105. In this embodiment, the inner basin 115 includes a floor 191 having a drain port 192 through which fluid can flow.

In this embodiment, the BSD 100 includes a propeller 130 coupled to a distal portion of the rotor 135. As explained in greater detail below, the propeller 130 can be rotated to urge fluids in the inner basin 115 through the drain port 192 and into an effluent plumbing assembly 160. The effluent plumbing assembly 160 includes at least one hemoconcentrating assembly for extracting red blood cells from the fluid for autotransfusion as described in greater detail below.

In this and other embodiments, one or more stabilizing members (not shown in FIG. 1) can assist in stabilizing the rotor 135 in a substantially vertical orientation as illustrated when the BSD 100 is in an operative configuration to extract blood from absorbent materials. In general, such an operative configuration can be one in which the inner basin 115 is filled to a desired level with rinse solution, the lid member 110 is sealingly engaged to the top portion 107 of the chamber 105 and the retaining basin 120 is in a lowered configuration in the inner basin 115 such that the absorbent materials contact the rinse solution.

Figure 2:
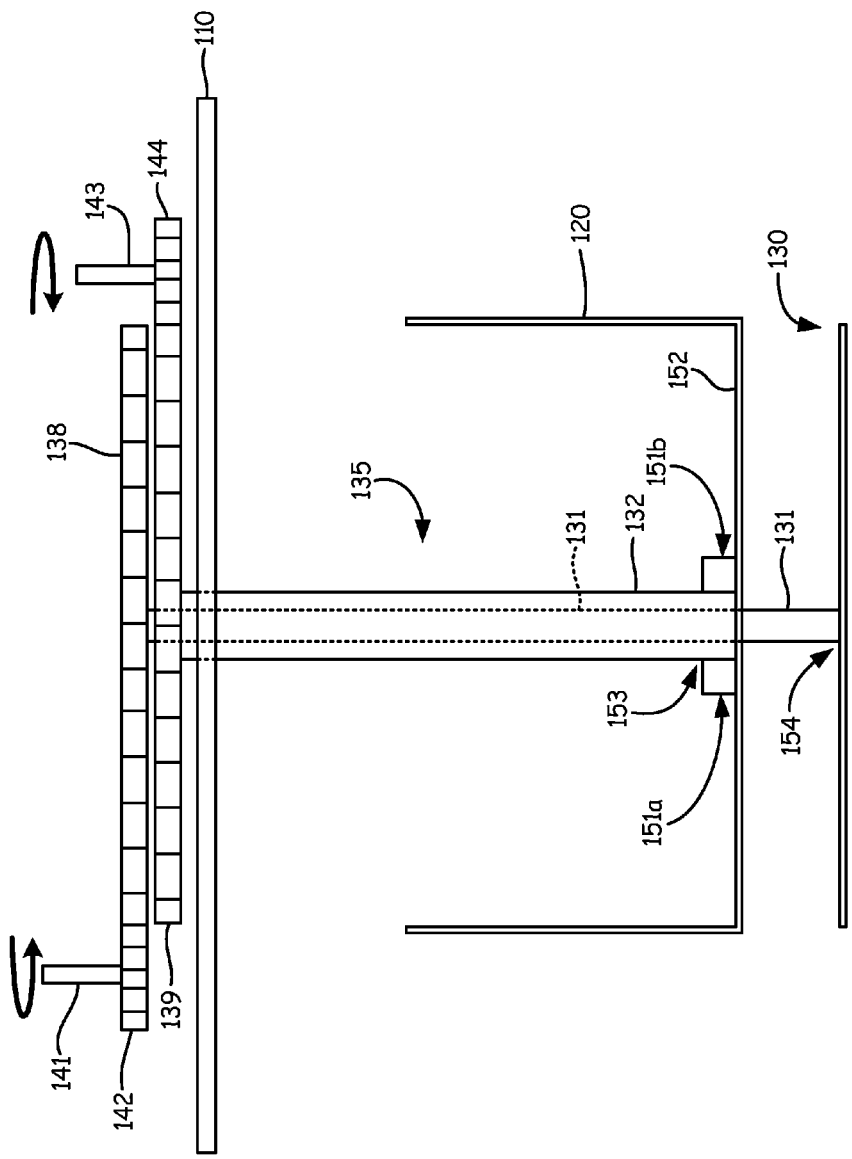
FIG. 2 illustrates a coaxial, dual-rotor assembly for use with a BSD, according to one embodiment.

Referring to FIG. 2, in general, the BSD 100 can be configured such that the retaining basin 120 and the propeller 130 can be rotated synchronously or independently. Such functionality can be accomplished, e.g., through use of a coaxial, dual-rotor assembly. FIG. 2 shows only selected components of the BSD 100 shown in FIG. 1 for figure clarity and are not to scale. In such an approach, rotor 135 can include a first, hollow rotor 132 rotationally driven by a first gear 139. The first gear 139 can be driven by a first output gear 144 coupled to an output shaft 143 of a first, controllable motor (not shown in FIG. 2). A distal portion 153 of the first, hollow rotor 132 is coupled to the retaining basin 120 via welds 151a, 151b to provide synchronous rotation of the retaining basked 120 as the first, hollow rotor 132 rotates. A second rotor 131 is disposed coaxially within the first hollow rotor 132 and is driven by a second gear 138. The second gear 138 can be driven by a second output gear 142 that is coupled to an output shaft 141 of a second, controllable motor (not shown in FIG. 2). A distal portion 154 of the second rotor 131 can be attached to the propeller 130 via welds, couplings, or other suitable attachment methods or devices that will be apparent to those skilled in the relevant art.

Such an embodiment can provide an advantageous configuration in which the first (132) and second (131) rotors are configured to rotate in opposite directions at a user-controllable angular velocity. Such an arrangement can enable the propeller 130 and the retaining basin 120 to rotate in opposite directions to improve stability and minimize gyroscopic forces created by the various rotating components, although such a configuration is not absolutely required. Furthermore, the speed at which the retaining basin 120 and propeller 130 rotate can be independently controlled so as to maximize fluid extraction and minimize hemolysis, respectively. Coaxaial dual-rotor assemblies are known in the mechanical arts, especially in the field of helicopters having two, counter-rotating blades to improve stability of the aircraft. One non-limiting example of such an assembly is described in U.S. Pat. No. 5,791,592 to Herbert M. Nolan et al., which is incorporated in its entirety herein by reference.

In general, a BSD 100 can be operated in one of several modes as described in greater detail below. In this embodiment, a user can choose a desired operating mode by selecting an effluent pathway in the effluent plumbing assembly 160; exemplary operational modes are described after the description of the effluent plumbing assembly 160 that follows. As used herein, "effluent" refers to a solution comprising rinse solution and blood and other materials extracted from the absorbent surgical or trauma materials. Generally, the effluent can be created in the inner basin 115 and retaining basin 120 as the absorbent materials are washed with rinse solution.

In this embodiment, fluid travel (effluent and diluent) from the inner basin 115 through the various components of the effluent plumbing assembly 160 described below is engendered by rotation of the propeller 130, although other suitable fluid-flow methods can be substituted as desired. For example, pumps or other mechanical devices for engendering similar fluid flow can be used, although it may be important to monitor such alternative methods for hemolysis. In this embodiment, rotation of the propeller 130 can urge effluent through the drain port 192 into a lower conical portion 117 of the inner basin 115. The urging force can be sufficient to cause adequate fluid pressure throughout the plumbing assembly 160 to maintain continuous effluent flow through a chosen circuit. The speed at which effluent flows through a chosen circuit can be user-controlled by adjusting the angular velocity of the propeller, e.g., by hand or using a variable-speed motor.

In this embodiment, the conical bottom portion 117 is in fluid communication with a three-way valve 118 capable of directing effluent toward one of three different fluid pathways. In this embodiment, a first fluid pathway is defined in part by lumen 126 which extends from the three-way valve 118 to a return lumen 168. The return lumen 168 is configured to expel effluent into the inner basin 115, thereby completing a fluid circuit as illustrated. The first fluid pathway can be used, e.g., in conjunction with a first operating mode, described in greater detail below.

In this embodiment, a second fluid pathway is defined in part by lumen 121, which extends between the three-way valve 118 and a hemoconcentrator assembly 122. The hemoconcentrator assembly 122 is capable of extracting red blood cells from the effluent and producing a red blood cell supply discharge into lumen 124 for further processing as described in greater detail below and a diluent solution. In this embodiment, diluent solution, e.g., effluent that remains after extraction of red blood cells, is directed to the return lumen 168 via lumen 123 so that it can be reused (recycled) as rinse solution in the inner basin 115. The second fluid pathway can be used, e.g., in conjunction with a second or third operating mode, described in greater detail below.

In this embodiment, a third fluid pathway includes drain lumen 119, which can be used to drain the inner basin 115 of its contents, e.g., rinse solution, blood, and other substances. Lumen 119 can be connected, e.g., at a distal end to a disposal container configured to receive bio-hazardous waste.

It should be understood that, with reference to the claims, terms such as "first," "second," and "third" fluid pathway as used in the description of drawings herein are not inextricably bound to the corresponding structure but are merely used for illustrative and descriptive purposes.

Figure 3:
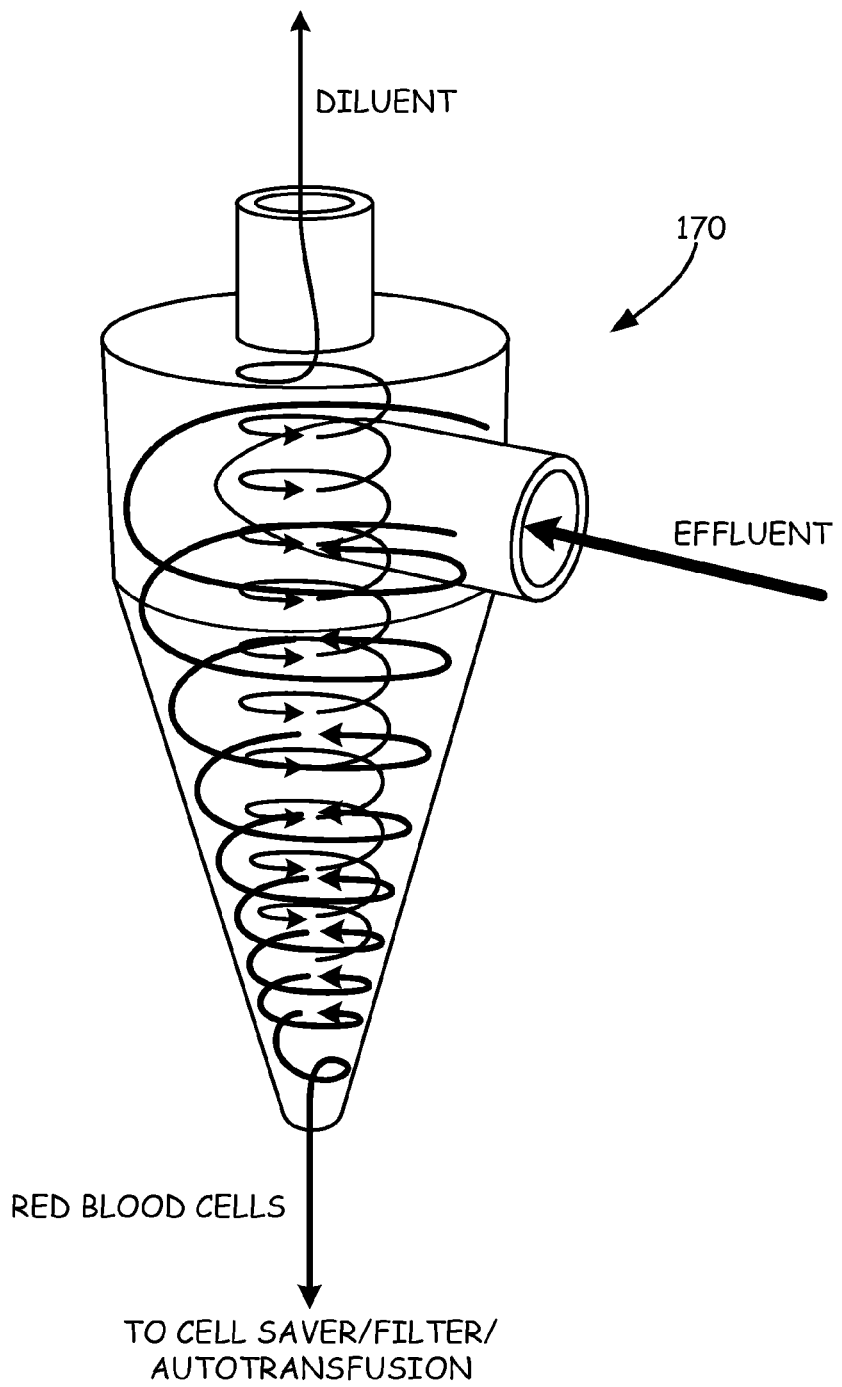
FIG. 3 illustrates a hydrocyclone-based particle separator, according to one embodiment.

Referring now to FIG. 3, in general, the hemoconcentrator 170 can be any device capable of extracting, filtering or concentrating red blood cells from the effluent. In a first preferred embodiment, the hemoconcentrator 170 is an ultrafiltration device, e.g., a Capiox™ HC11 or HC05 Hemoconcentrator, produced by Turomo Cardiovascular Systems Corp., Ann Arbor, Mich. In second preferred embodiment, the hemoconcentrator 170 is a hydrocyclone-based particle separator; such types of separators are capable of receiving an effluent mixture of red blood cells and rinse solution and substantially separating each component using cyclonic separation. In this embodiment, the hydrocyclone-based particle separator produces two outputs, a red blood cell supply discharge and a diluent discharge, wherein the later includes mostly rinse solution, substantially devoid of red blood cells, e.g., the diluent. The diluent can be recycled for further blood extraction, thereby reducing the amount and cost of needed rinse solution. Hydrocyclone-based separator devices are known in the art and described, e.g., in T. Dyakowski, A. F. Nowakowski, W. Kraipech and R. A. Williams, "*A Three Dimensional Simulation of Hydrocyclone Behavior*," Second International Conference on CFD in the Minerals and Process Industries, SCIRO, Melbourne, Australia, 6-8 Dec. 1999, pp. 205-210.

In general, the physical characteristics of the hydrocyclone-based separator, e.g., the body size, shape, including conical dimensions, etc., and the velocity of fluid flowing therethrough can influence the efficiency and effectiveness of particle separation. Thus, it should be understood that while hydrocyclone-based separators are referred to in a general sense herein, one which specifically takes into account the size, weight, density, and other physical factors of red blood cells can be advantageous in a BSD 100 to maximize recovery of red blood cells for autotransfusion. In one embodiment, the BSD can include a feedback system that monitors the collection of viable red blood cells from the system and adjusts parameters of its operation, e.g., fluid velocity through the hemoconcentrator, to effect maximum efficiency.

In this embodiment, a first BSD 100 operating mode is one that provides a basic rinse of absorbent surgical or trauma materials, e.g., sponges 125, prior to disposal. This first mode can be used as a front line safety practice to minimize biohazard exposure risk to surgical staff, particularly when there is a known infectious agent present. In this mode, a rinse solution can be applied to the absorbent surgical or trauma materials within the retaining basin 120, e.g., by soaking, submerging, or showering. In one of many approaches, the rinse solution can contain a broad spectrum antimicrobial agent to kill bio-hazardous substances.

In an optional step, the propeller 130 can be activated, e.g., by hand rotation or via a motor, if so equipped, so as to produce a flow of effluent through the aforedescribed fluid circuit. Such action may increase the extraction of blood and other contaminants from the absorbent surgical or trauma materials. After soaking, the retaining basin 120 can be raised above any standing rinse solution and spun to drive blood and rinse solution from the absorbent surgical or trauma materials by way of centrifugal force. During the spin cycle, the lid 110 should be in a closed, sealed configuration to minimize the likelihood of blood escaping the BSD 100 and contacting persons in the vicinity. After an appropriate amount of time, the absorbent surgical or trauma materials can be removed from the retaining basin 120 and discarded according to any standing biohazard disposal protocols. Effluent, e.g., rinse solution, blood, etc., will be contained in the retaining basin 115 and may be discarded by adjusting the three-way valve 118 into a configuration that directs the effluent along the aforedescribed third fluid pathway, e.g., toward drain lumen 119.

In this embodiment, a second BSD 100 operating mode is one that recovers blood cells from the absorbent surgical or trauma materials. In this mode, the inner basin 115 can be filled with rinse solution such that about one-half (the bottom half) of the retaining basket 120 is submerged. (The filling process also allows rinse solution to enter and fill the effluent plumbing assembly 160.) In one embodiment, a fitting such as a Luer Lock™ connector can extend from the interior of the inner basin 115 to the outside of the outer chamber 105, enabling a user to fill the inner basin 115 with rinse solution without opening the lid 110. Other approaches to achieve the same functionality can be used and will be apparent to skilled artisans. The blood-soaked absorbent surgical or trauma materials can be placed in the retaining basin 120. A selected amount of rinse solution, e.g., one containing heparinized saline, can be applied to the absorbent surgical or trauma materials. The application of rinse solution can be accomplished, e.g., by pouring an adequate amount of rinse solution to cover the absorbent surgical or trauma materials, by a shower application, or any other desired method. The rinse solution will be held by the inner basin 115. Next, the retaining basin 120 and propeller 130 can be spun, e.g., by hand or via a motor, if so equipped, to wash the absorbent surgical materials and urge effluent containing blood and other fluids out of the retaining basin 120 and into the inner basin 115. As previously described, rotation of the propeller 130 can urge effluent flow into the conical portion 117 and toward the three-way valve 118.

In the second BSD 100 operating mode, the three-way valve 118 can be adjusted to allow effluent to flow into the aforedescribed second fluid pathway, e.g., into lumen 121. Effluent is then directed into the hemoconcentrator 122 to separate red blood cells from the rinse solution. Diluent from the hemoconcentration process, e.g., rinse solution remaining after red blood cell extraction, is directed via lumen 123 to a return lumen 168 and back into the inner basin 115 to provide further rinsing of the absorbent surgical or trauma materials. A red blood cell discharge from the hemoconcentrator 122 is directed via lumen 124 to a two-way valve 127.

In this embodiment, in the second BSD 100 operating mode, a user can choose to direct the red blood cell discharge from the hemoconcentrator into a cell salvaging machine, illustrated by box 128, by appropriate adjustment of the two-way valve 127. FIG. 1 illustrates the red blood cell discharge flow pathway using arrows for simplicity, however, it should be understood that any plumbing and connection methods can be used to provide fluid communication between the two-way valve 127 and a cell salvage machine 128. One exemplary cell salvage machine that can be used in conjunction with a BSD 100 is provided by Haemonetics Corp. of Braintree, Mass., and sold under the "Cell Saver"™ trade name. Blood processed by the Cell Saver device can then be flowed to the patient, illustrated by box 146.

In a third operating mode, the BSD 100 can be configured to produce a supply of processed, sterilized red blood cells for autotransfusion without the use of a cell salvage machine 128. In this operating mode, the red blood cell supply discharge from the hemoconcentrator 122 is directed toward a microporous membrane blood filter 147 to remove any remaining potentially-harmful biologic substances or debris from the red blood cell supply discharge. Next, the filtered blood is allowed to percolate through a de-heparinization chamber 148 containing, e.g., chitosan microspheres or other positively charged porous polymer material to remove remaining heparin. The resulting filtrate includes red blood cells that are substantially free of biological and chemical contaminants, and can be safely autotransfused into the patient 146.

In a fourth operating mode, the BSD 100 can extract red blood cells from absorbent surgical or trauma materials and additionally purify and sterilize the blood cells for direct autotransfusion. Such a configuration can be used with any other of the described embodiments, including variations thereof. However, the fourth operating mode can be particularly advantageous for direct recovery of red blood cells from open or enteric contaminated wounds, e.g. abdominal trauma involving the intestines, bladder, liver, spleen or gall bladder. In this operating mode, blood from such wounds or surgical sites can be introduced directly into the chamber 105 using, e.g., a suction device attached to one of the plurality of suction ports 150. Blood introduced into the chamber in this way can enter the retaining basin 120 and inner basin 115 via gravity and mix with rinse solution therein. Although blood can be directly introduced into the BSD 100 using a suction tool, it does not preclude simultaneous extraction of blood from blood-soaked absorbent materials as described herein.

Figure 4:
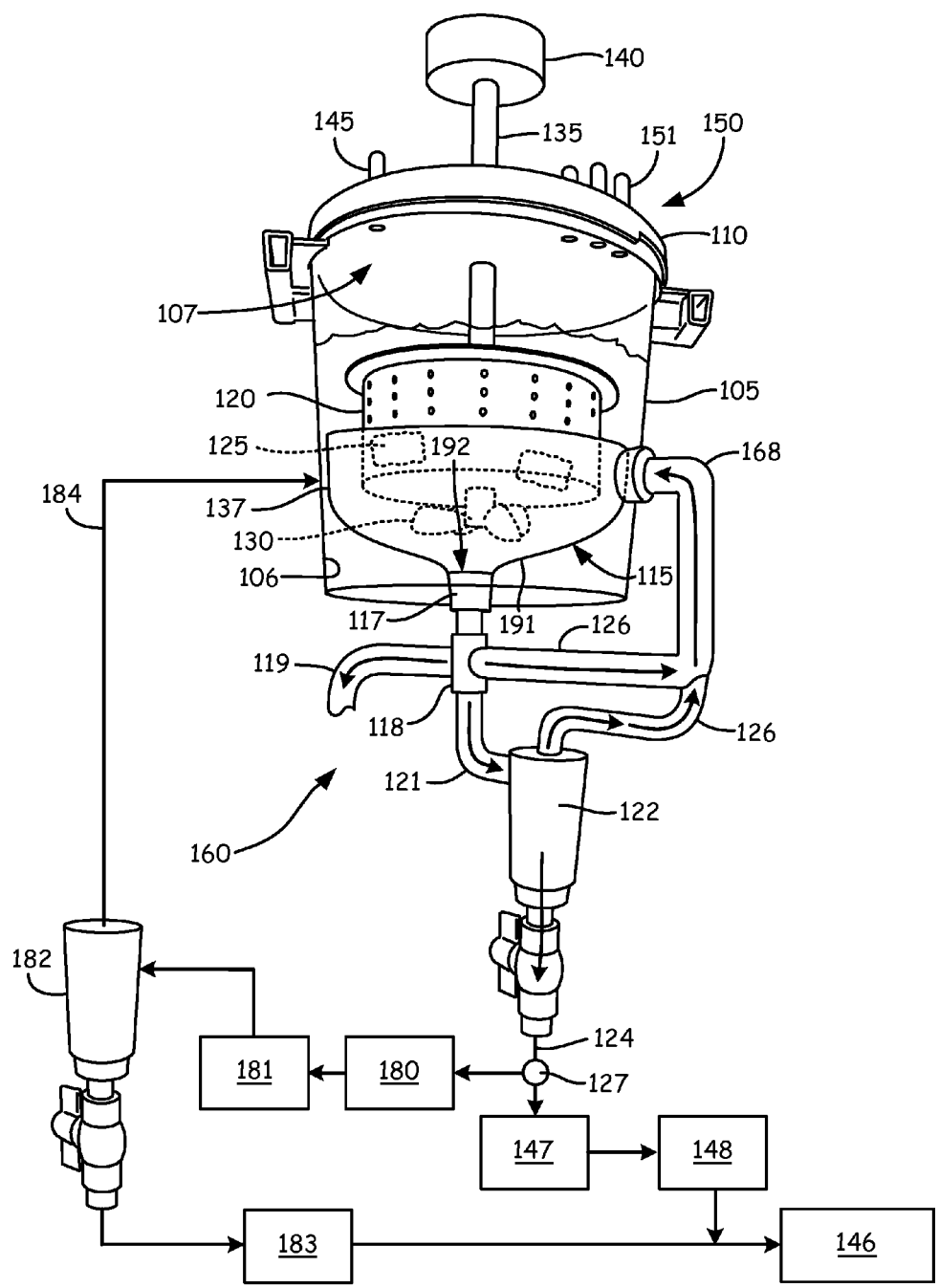
FIG. 4 illustrates a blood salvage device according to one embodiment.

Referring now to FIG. 4, the fourth operating mode can utilize an alternative embodiment of a BSD 100 having additional modules for purifying and sterilizing red blood cells for direct autotransfusion. It should be understood that the description and use of purification and sterilization modules that follows is not limited to the instant fourth operating mode; indeed, the following can be used with, or incorporated into any other embodiment or operating mode of a BSD.

In this alternative embodiment, the BSD 100 includes a dilution chamber 180 which receives the red blood cell supply discharge from the hemoconcentrator 122. (The Cell Saver device 128 is removed from FIG. 4 for clarity.) The dilution chamber 180 can dilute the concentration of red blood cells, e.g., by adding additional rinse or saline solution. In this alternative embodiment, the dilution chamber 180 increases the average space around each red blood cell to both ensure adequate exposure to radiation in the module that follows, and to reduce the likelihood of producing blockages in the following modules and connecting lumens.

In this alternative embodiment, the dilute red blood cell solution flows via lumen from the dilution chamber 180 to a sterilization chamber 181. In this alternative embodiment, the sterilization chamber 181 includes a UV light-transmissive cell through which the red blood cell solution flows. An ultraviolet (UV) light source is configured in the sterilization chamber 181 to produce a biocidal dose of radiation through the cell as the red blood cell solution flows through. In this arrangement, the UV light can kill harmful bacteria or other organisms that may be present in the red blood cell solution. Without wishing to be bound by theory, such an arrangement can be advantageous in reducing the likelihood of infection or other disease, particularly from drug- and antibiotic-resistant microorganisms. One example of blood sterilization using UV-C light is described in U.S. Pat. No. 6,193,681 to A. Davidner et al., filed Sep. 14, 1998, which is incorporated herein in its entirety by reference.

In this alternative embodiment, the red blood cell solution flows via lumen from the sterilization chamber 181 to a second hemoconcentrator 182. In this alternative embodiment, the second hemoconcentrator 182 is a second hydrocyclone particle separator; however, any suitable hemoconcentrator can be substituted according to preference or performance factors. In this alternative embodiment, the diluent that flows from the second hemoconcentrator 182 is flowed via lumen 184 back into the inner basin 115 to be used again.

In this alternative embodiment, a second red blood cell supply discharge flows via lumen from the second hemoconcentrator 182 to a deheparinzation chamber 183 to remove heparin. Subsequently, the sterilized, concentrated, and de-heparinized red blood cell supply can be autotransfused into the patient 146.

In the foregoing alternative embodiment, any type of lumen or other plumbing components can be used to interconnect the various modules, e.g., Tygon™ tubing, PVC piping, silicone or polyethylene tubing can be used, as will be apparent to those skilled in the art.

In this and other embodiments, it can be advantageous to use the shortest lengths of the smallest diameter plumbing materials (lumens, connectors, etc.) possible to interconnect the various components of a BSD to reduce the amount of rinse solution needed for efficient effluent flow while maintaining desired functionality.

Figure 5:
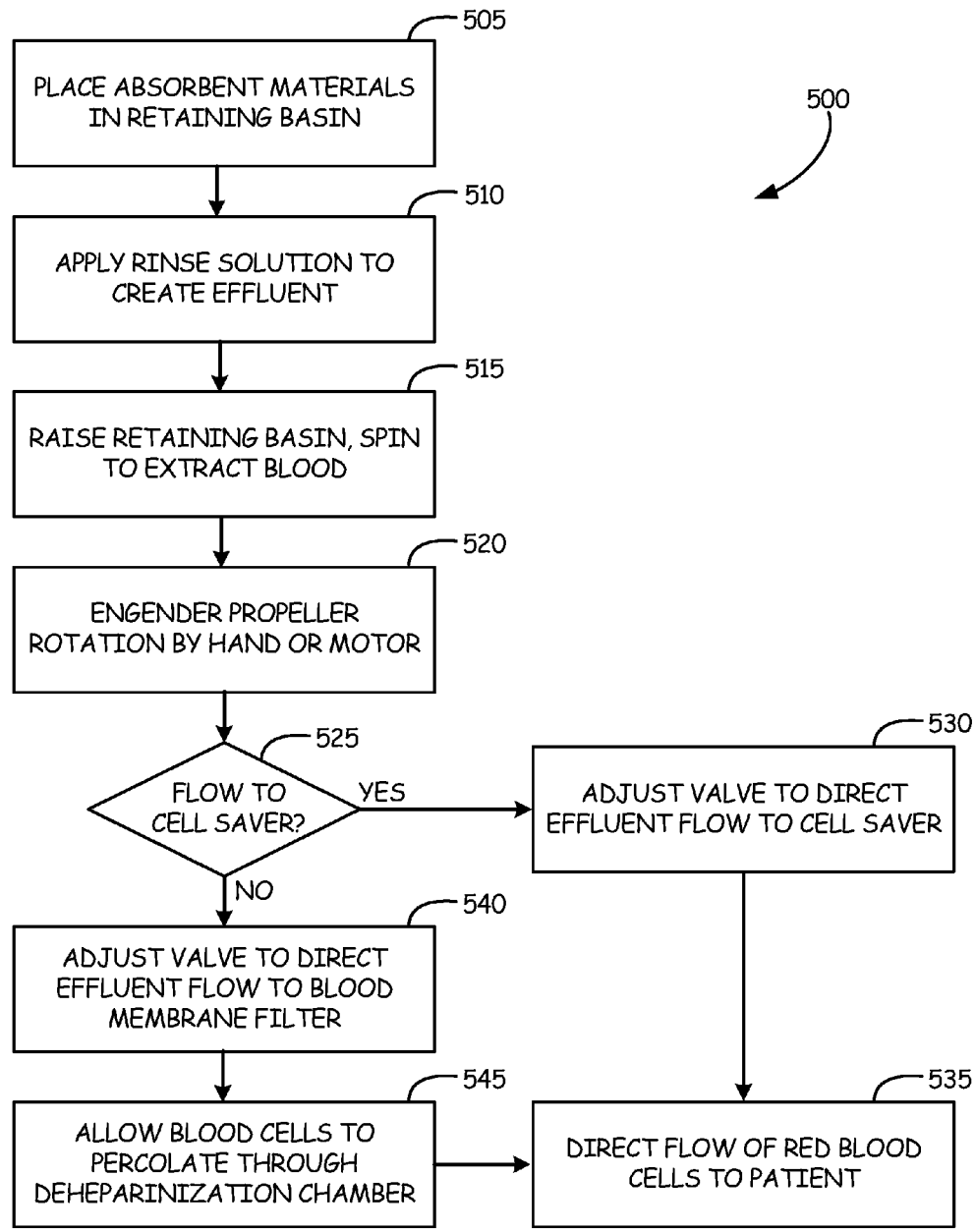
FIG. 5 is a flowchart of method for salvaging red blood cells for autotransfusion, according to one embodiment.

In general, methods for recovering patient blood from absorbent materials are disclosed. Referring now to FIG. 5, a flowchart 500 illustrates steps for recovering patient blood from absorbent materials according to one embodiment. Reference is made to the BSD 100 shown in FIG. 1 for illustrative purposes.

Beginning at step 505, a user can place absorbent surgical or trauma materials, e.g., sponge 125 having blood contained therein into the retaining basin 120. The lid 110 can be closed and sealed against the outer chamber 105 to prevent fluids from escaping the BSD during processing.

Next, at step 510, the absorbent surgical or trauma materials can be exposed to a rinse solution such as saline or heparinized saline, for example. In some cases, the inner basin 115 can be pre-filled with rinse solution; in other cases, the rinse solution can be applied in a shower-like fashion over the absorbent materials. The retaining basin 120 can be spun by hand or motor, creating a centrifugal-like bath that extracts blood from the absorbent materials. In one approach, the spinning motion can be started and stopped several times to maximize blood extraction from the absorbent materials. As the retaining basin 120 is spun, a vortex of effluent (rinse solution plus blood and other liquids extracted from the absorbent materials) can be created in the inner basin 115. The effluent vortex may be pushed up the inner wall 106 of the chamber 105 such that it no longer contacts the retaining basin 120.

Next, at step 515, the retaining basin 120 can be raised out of the effluent (which may still be spinning in vortex-like fashion) and spun until the absorbent materials appear substantially free of rinse solution. In some embodiments, the propeller 130, retaining basin 120, and rotor 135 can be configured so that the propeller remains substantially near the bottom of the inner basin 115 when the retaining basin 120 is shifted upward, out of the rinse solution as just described.

Next, at step 520 the propeller 130 is engendered to rotate by hand or motor, although in many cases, the propeller 130 may already be rotating from the process of spinning the retaining basin 120 described in step 415. However, rotation of the propeller 130 can drive fluid through the effluent plumbing assembly 160 to both recover viable red blood cells and drive recycled rinse solution back into the inner basin 115.

Effluent travels from the inner basin 115 to the hemoconcentrator 122 (in this example, a hydrocyclone particle separator) via lumen 121. The particle separator will separate red blood cells from the rinse solution as previously described. The diluent (that left over from the extraction of red blood cells from the effluent) is directed back to the inner basin 115 as previously described to be recycled. A red blood cell supply discharge is directed toward two-way valve 127 and contains red blood cells extracted from the effluent.

Next, decision 525 relates to whether the user desires to use an accessory cell salvaging machine such as the aforementioned Cell Saver™ device. If so, at step 530 the two-way valve can be adjusted to direct effluent flow toward the Cell Saver for processing. The resulting red blood cells can then be directed to the patient for autotransfusion, step 535.

Returning to decision 525, if the user does not desire use of a cell salvaging machine, the two-way valve 118 can be adjusted to direct the red blood cell supply discharge flow to the blood membrane filter 440 (step 540) which filters out any contaminates still present in the effluent after running through the hydrocyclone particle separator.

Next, at step 545, filtered red blood cell supply discharge is percolated through a de-heparinization chamber to remove any remaining heparin from the rinse solution.

Finally, at step 535, purified red blood cells can be directly autotransfused into the patient.

EXAMPLE

The success of autotransfusion can depend on viable recovered red blood cells; generally, the breaking or lysing of red blood cells in the recovery process should be minimal in order to ensure patient safety. In one study, the performance of a BSD similar to that described herein was characterized in terms of processing efficacy and the recovery rate of intact red blood cells from absorbent surgical material. The level of hemolysis can be determined by examining the indicators in Table 1. An 80% recovery of intact red blood cells was considered to be acceptable according to some industry standards.

A blood salvage device similar to that described above with respect to FIG. 1 was tested using 300 mL test units of recently expired (within 24 hours of test) human packed red blood cells (American Red Cross, St. Paul, Minn.) diluted in 7 liters of 0.9% NaCl (normal saline) containing 50,000 units of heparin sulfate. Each test (i.e., Test #1, Test #2 in Table 1) included placing twelve 4 inch×8 inch surgical gauze sponges in the porous retaining basin and rotating the basin at approximately 300 rpm for 8 and 9 minutes, respectively (time required for sponges to appear essentially free of blood). Samples were collected at an exit port after passing through a hydrocyclone hemoconcentrator (Rusco™ 2-1000-F 1000 Mesh 2 Spin-Down Polyester Sedimentation Filter with Flush Valve, Rusco Sediment Filters, Brooksville, Fla.). Pre-run samples (red top BD Vacutainer™ Blood Collection Tube) were obtained immediately following dilution. Post-run samples were obtained immediately following solution collection. Samples were analyzed for key indicators of hemolysis at Allina Health Laboratory, Minneapolis, Minn.

TABLE 1

Key hemolysis indicators after human packed red blood cells separated from blood soaked surgical sponges in red blood cell recovery device.

| Hemolysis indictor | Test # 1 | | | Test #2 | | |
|---|---|---|---|---|---|---|
| | Pre-run | Post-run | % Change | Pre-run | Post-run | % Change |
| Plasma Free HGB (mg/dL) | 3.0 | 4.0 | 33 | 3.0 | 4.0 | 33 |
| K+ (mmmol/L) | 1.1 | 1.1 | 0.0 | 1.1 | 1.1 | 0.0 |
| LDH (U/L) | <30 | <30 | 0.0 | <30 | <30 | 0.0 |
| HGB (mg/dL) | 0.7 | 0.7 | 0.0 | 0.8 | 0.8 | 0.0 |
| HCT (%) | 2.2 | 2.1 | −4.5 | 2.5 | 2.9 | 16 |

Referring to Table 1, the low level of plasma-free Hgb (a sensitive measure of hemolysis) indicates that the BSD device can recover viable blood cells for autotransfusion with proficiency.

A number of illustrative embodiments have been described. Nevertheless, it will be understood that various modifications may be made without departing from the spirit and scope of the various embodiments presented herein. For example, the basins described herein can be composed of any suitable or desirable material, including, but not limited to plastics, glass, metals, etc. In a preferred embodiment, the basin can be formed from resilient Plexiglas to reduce the likelihood of breakage. Various types of motors can be used in embodiments that extract blood from absorbent materials using centrifugal force, including electric and variable-speed electric motors. Substantially cylindrical basins are depicted in the various drawings for simplicity; it will be understood that the basin can be of any desired shape or size to suit the user or provide advantages in manufacturing of the various systems described herein. Similarly, basins can be configured or shaped according to preference or manufacturing considerations while still providing the same or similar functionality. Temperature control of blood salvaged from absorbent materials using the systems described herein can be achieved by a variety of methods. In one example, the chamber 105 can include a temperature control assembly that includes heating or cooling elements and thermocouples or other sensors for measuring the temperature of collected blood and fluids. It will be understood that the drawings presented herein may not be to scale and that various modifications and improvements can be made without departing from the spirit and scope of their intended use. Accordingly, other embodiments are within the scope of the following claims.

What is claimed is:

1. An assembly for salvaging blood cells from an absorbent material, comprising:
    a first basin having perforations to allow a rinse solution to wash said blood cells from said absorbent material into a second basin to form an effluent solution;
    an elongate rotor having a first rotor portion fixedly attached to a center of mass of said first basin that defines an axis of rotation about which said first basin can axially rotate; and
    a hemoconcentrator in fluid communication with said second basin having first and second fluid outputs for discharging a diluent solution and a blood cell discharge solution from said effluent solution respectively;
    wherein said first fluid output is in fluid communication with said second basin for recycling said diluent solution as said rinse solution.

2. The assembly of claim 1, wherein said hemoconcentrator is a hydrocyclone-based particle separator.

3. The assembly of claim 1, wherein said first basin is rotatable.

4. The assembly of claim 1, wherein a lumen-interconnected fluid flow circuit is defined by said second basin, said hemoconcentrator, back to said second basin, wherein said fluid flow is engendered by a pump.

5. The assembly of claim 1, wherein said first fluid output of said hemoconcentrator is in fluid communication with an intraoperative cell salvage machine.

6. The assembly of claim 1, further comprising a handle coupled to a proximal portion of said elongate rotor configured to engender rotation of said first basin when said handle is rotated.

7. The assembly of claim 1, further comprising a motor configured to rotate said rotor about said axis of rotation.

8. The assembly of claim 1, further comprising a propeller fixedly coupled to a distal end of said rotor that is configured to flowingly urge said effluent solution in said second basin to said hemoconcentrator.

9. The assembly of claim 1, wherein said first basin is capable of reversibly shifting along said axis of rotation to reversibly remove said absorbent materials from said rinse solution.

10. The assembly of claim 8, wherein said first basin and said propeller are configured to be selectably rotatable in the same or opposite rotation directions.

11. The assembly of claim 8, wherein the rotation speed of each of said first basin and said propeller are independently controllable.

12. The assembly of claim 8, wherein said rotor is a coaxial dual-rotor assembly having an inner rotor and an outer rotor each capable of independent, coaxial rotation, and wherein said inner rotor is coupled to said first basin or said propeller, and said outer rotor is coupled to said first basin or said propeller.

13. The assembly of claim 1, further comprising a valve member in fluid communication with said first fluid output of said hemoconcentrator, operable to direct said blood cell discharge solution into one of a plurality of fluid flow passages, wherein:
    a first fluid flow passage is configured to flow said blood cell discharge solution from said valve member to an intraoperative cell salvaging machine.

14. The assembly of claim 13, wherein a second fluid flow passage is configured to flow said blood cell discharge from said valve member to a filter capable of removing impurities from said blood cell discharge solution.

15. The assembly of claim 14, wherein said second fluid flow passage further comprises an in-line de-heparinization chamber for removing heparin, if present, from said blood cell discharge solution downstream from said blood filtering device.

16. The assembly of claim 1, further comprising a chamber having a reversibly sealable lid member, wherein said chamber is configured to substantially enclose said first basin and said second basin.

17. The assembly of claim 16, wherein said lid member comprises a vacuum port cooperatively operable with a vacuum source to lower the atmospheric inside said chamber when said lid is in a sealed configuration.

18. The assembly of claim 17, wherein said lid member further comprises one or more accessory suction ports configured to couple to a suction device for vacuuming blood into said chamber.

19. The assembly of claim 16, wherein said lid further comprises a perforated, annular and circumferential lumen configured to receive said rinse solution and produce a flow of said rinse solution substantially along the inner walls of said chamber.

20. An assembly for salvaging blood for direct patient autotransfusion, comprising:
   a wash basin configured to retain a volume of blood-releasing rinse solution and house a portion of a perforated basin for receiving absorbent materials comprising said patient's blood;
   a hemoconcentrator assembly in fluid flow communication with said wash basin capable of substantially separating red blood cells of said patient's blood from said rinse solution to form a first red blood cell discharge solution comprising said red blood cells and a first diluent solution comprising said rinse solution, wherein said fluid flow between the wash basin and the hemoconcentrator assembly is engendered by a propeller operatively disposed within said wash basin; and
   a disinfection chamber in fluid flow communication with said hemoconcentrator configured to receive said red blood cell discharge solution, and comprising a light source capable of emitting an effective dose of electromagnetic radiation to substantially sterilize said red blood cell discharge solution.

21. The assembly of claim 20 wherein said fluid flow between the wash basin and the hemoconcentrator assembly is further engendered by a pump.

22. The assembly of claim 20, wherein said perforated basin is rotatable, and said propeller is coupled to a first portion of a rotor that extends through, and is coupled to a center of gravity of said perforated basin at a second, different portion of said rotor so that said propeller and said rotatable perforated basin share a common axis of rotation.

23. The assembly of claim 20, wherein said first diluent solution is flowed via a first lumen to the wash basin for re-use as said rinse solution.

24. The assembly of claim 20, wherein said light source is capable of emitting ultraviolet light.

25. The assembly of claim 20, further comprising a dilution chamber in fluid communication between said hemoconcentrator and said disinfection chamber for diluting the concentration of red blood cells in said red blood cell discharge solution.

26. The assembly of claim 20, further comprising a second hemoconcentrator in fluid communication with said disinfection chamber that is configured to receive said sterilized red blood cell discharge solution, and further configured to create a second red blood cell supply discharge solution and a second diluent solution from said sterilized red blood cell discharge solution, wherein said second diluent solution is in fluid communication with said wash basin.

27. The assembly of claim 20, wherein said hemoconcentrator is a hydrocyclone-based particle separator.

28. An assembly for salvaging a patient's blood cells from a blood source, comprising:
   a rotatable, perforated basin for receiving blood from said blood source;
   an elongate rotor extending through, and coupled to a center of gravity of said rotatable perforated basin;
   a propeller coupled to a distal end of said rotor;
   a wash basin capable of receiving said propeller and at least a portion of said rotatable, perforated basin therein, wherein said wash basin is also configured to retain a volume of rinse solution, wherein said rinse solution is capable of forming an effluent solution comprising said blood cells in suspension;
   a housing for enclosing said wash basin, said propeller, and said perforated basin configured to receive a reversibly sealable lid member through which a proximal end of said rotor extends to couple to a motor or hand crank for spinning said propeller and said rotatable perforated basin; and
   a hydrocyclone-based particle separator in fluid-flow communication with said wash basin that is configured to separate said effluent solution into a red blood cell discharge solution comprising said red blood cells and a diluent solution comprising rinse solution;
   wherein said red blood cell discharge solution can be salvaged for autotransfusion; wherein said diluent solution is in fluid communication with said wash basin via one or more lumen passages to be re-used as said rinse solution; and wherein said propeller is capable of engendering said fluid flow.

* * * * *